United States Patent
Raeymaekers et al.

(10) Patent No.: US 9,872,772 B2
(45) Date of Patent: Jan. 23, 2018

(54) PROSTHETIC JOINT

(71) Applicant: University of Utah Research Foundation, Salt Lake City, UT (US)

(72) Inventors: Bart Raeymaekers, Salt Lake City, UT (US); Anthony Sanders, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/412,630

(22) PCT Filed: Jul. 2, 2013

(86) PCT No.: PCT/US2013/049115
§ 371 (c)(1),
(2) Date: Jan. 2, 2015

(87) PCT Pub. No.: WO2014/008284
PCT Pub. Date: Jan. 9, 2014

(65) Prior Publication Data
US 2015/0148910 A1 May 28, 2015

Related U.S. Application Data

(60) Provisional application No. 61/667,146, filed on Jul. 2, 2012.

(51) Int. Cl.
A61F 2/32 (2006.01)
A61F 2/30 (2006.01)
(Continued)

(52) U.S. Cl.
CPC ............ *A61F 2/30771* (2013.01); *A61F 2/32* (2013.01); *A61F 2/34* (2013.01); *A61L 27/04* (2013.01);
(Continued)

(58) Field of Classification Search
None
See application file for complete search history.

(56) References Cited

U.S. PATENT DOCUMENTS 5,037,438 A 8/1991 Davidson
5,197,987 A 3/1993 Koch et al.
(Continued)

OTHER PUBLICATIONS

Etsion, I. "Improving Tribological Performance of Mechanical Components by Laser Surface Texturing." Tribology Letters, vol. 17, No. 4, Nov. 2004: 733-737.*
(Continued)

*Primary Examiner* — Thomas J Sweet
*Assistant Examiner* — Megan Wolf
(74) *Attorney, Agent, or Firm* — Thorpe North & Western, LLP

(57) ABSTRACT

A prosthetic joint (100) comprises a first component (110) having a first interface portion (111). The prosthetic joint (100) further comprises a second component (120) having a second interface portion (121) with a textured surface (122) to interface with the first interface portion (111) and form a skeletal joint. The textured surface (122) can include a plurality of concave features (123). Each or the concave features (123) can be configured to compress a lubricant (140) to facilitate hydrodynamic lubrication between the first and second interface portions (111, 121) to minimize wear between the first interface portion (111) and the second interface portion (121) of the prosthetic joint (100).

18 Claims, 4 Drawing Sheets

(51) Int. Cl.
*A61L 27/04* (2006.01)
*A61L 27/10* (2006.01)
*A61L 27/50* (2006.01)
*A61L 27/34* (2006.01)
*A61F 2/34* (2006.01)

(52) U.S. Cl.
CPC ............ *A61L 27/10* (2013.01); *A61L 27/105* (2013.01); *A61L 27/34* (2013.01); *A61L 27/50* (2013.01); *A61F 2002/30673* (2013.01); *A61F 2002/30784* (2013.01); *A61F 2002/30805* (2013.01); *A61F 2002/30807* (2013.01); *A61F 2002/30934* (2013.01); *A61L 2400/10* (2013.01); *A61L 2430/24* (2013.01)

(56) References Cited

U.S. PATENT DOCUMENTS

| | | | |
|---|---|---|---|
| 5,462,362 A | 10/1995 | Yuhta et al. | |
| 5,834,094 A * | 11/1998 | Etsion | F16C 33/14 277/301 |
| 5,879,406 A | 3/1999 | Lilley | |
| 5,916,269 A | 6/1999 | Serbousek et al. | |
| 6,045,581 A * | 4/2000 | Burkinshaw | A61F 2/32 623/18.11 |
| 6,045,584 A | 4/2000 | Benzel et al. | |
| 6,425,921 B1 * | 7/2002 | Grundei | A61F 2/30771 623/18.11 |
| 6,645,251 B2 | 11/2003 | Salehi et al. | |
| 6,660,040 B2 * | 12/2003 | Chan | A61F 2/30771 623/22.11 |
| 8,323,349 B2 | 12/2012 | Schmid | |
| 2003/0060891 A1 | 3/2003 | Shah | |
| 2003/0114935 A1 | 6/2003 | Chan et al. | |
| 2005/0182494 A1 * | 8/2005 | Schmid | A61F 2/30771 623/23.5 |
| 2006/0184251 A1 | 8/2006 | Zhang et al. | |
| 2007/0270975 A1 * | 11/2007 | Taylor | A61F 2/30771 623/23.5 |
| 2008/0071381 A1 | 3/2008 | Buscher et al. | |
| 2008/0221680 A1 | 9/2008 | Hodorek | |
| 2009/0112330 A1 | 4/2009 | Grundei | |
| 2009/0125108 A1 | 5/2009 | Linares | |
| 2010/0063589 A1 | 3/2010 | Tepic | |
| 2012/0203351 A1 * | 8/2012 | Thompson | A61F 2/32 623/22.15 |
| 2012/0221110 A1 | 8/2012 | Nakanishi et al. | |

OTHER PUBLICATIONS

Hiroshi et al., Reduction of Polyethylene Wear by Concave Dimples on the Frictional Surface in Artificial Hip Joints, The Journal of Arhtroplasty vol. 15, No. 3, Jun. 2, 1999, 332-338.

Raeymaekers et al., Enhancing Tribological Performance of the Magnetic Tape/Guide Interface by Laser Surface Texturing, Tribology Letters, 27 (1), Feb. 20, 2007, 89-95.

Raeymaekers et al., A Model for Magnetic Tape/Guide Frictin Reduction by Laser Surface Texturing, Tribology Letters 28, Jun. 11, 2007, 9-17.

Izhak, Etsion, State of the Art in Laser Surface Texturing, Journal of Tribology, vol. 127, Jan. 2005, 248-253.

PCT Application No. PCT/US2013/049115, Filing Date Jul. 2, 2013, Bart Raeymaekers, International Search Report, dated Nov. 20, 2013, 12 Pages.

* cited by examiner

PROSTHETIC JOINT

RELATED APPLICATION

This application claims priority to U.S. Provisional Patent Application No. 61/667,146, filed Jul. 2, 2012 which is incorporated herein by reference.

BACKGROUND

More than 200,000 total hip replacement (THR) surgeries are performed in the U.S. each year. Such surgery is needed when the cartilage cushioning of the joint deteriorates (osteoarthritis), causing pain and disability. The statistical survivorship of THR devices declines dramatically after ten years of use, and few reach 15 years of useful life because the sliding interface between the femoral head (usually CoCr) and the acetabular cup/liner (usually Ultra High Molecular Weight Polyethylene (UHMWPE), or cross-linked polyethylene (XLPE)) breaks down or wears excessively. This lack of durability results from wear of the prosthetic device, which has unacceptable effects, such as riskier revision surgery or surgery postponement with its attendant pain and disability. Typical prosthetic devices have smooth bearing surfaces. In fact, the current engineering paradigm for combating implant wear is to manufacture smoother bearing surfaces.

Several types of bearings for THR devices exist: ceramic-on-ceramic (COC), ceramic-on-metal, ceramic-on-polyethylene, metal-on-metal, and metal-on-polyethylene (MOP). Femoral heads are thus typically either made of metal or ceramic material. Metal heads, often made of cobalt-chromium for hardness and fatigue resistance, are machined to size and then polished to reduce wear of the socket liner. Ceramic heads are typically smoother than polished metal heads, which enables them to operate in the hydrodynamic lubrication regime, thus reducing wear. Despite this advantage, COC hips are prone to edge-loading wear that leads to squeaking, problems that for instance MOP bearings do not exhibit. To date, the potential of also creating fluid film lubrication in MOP devices has been neglected, likely because the polymer bearing is compliant, prone to dimensional error, and not feasible to polish.

Particles generated by adhesive wear, corrosive wear, and/or abrasive wear can also act as abrasives and accelerate deterioration of the sliding interface. Additionally, adverse immunological reaction to indigestible microscopic wear debris can lead to osteolysis, which can undermine the implant and cause instability, which is a leading cause of revision surgery. Thus, preventing or significantly reducing formation of wear particles in the sliding interface between the acetabular component and the femoral head is an ongoing challenge.

SUMMARY

Thus, there is a need for a prosthetic joint capable of providing reduced friction and wear. Accordingly, a unique prosthetic joint and associated methods are provided. Such a joint can comprise a first component having a first interface portion. The prosthetic joint can also comprise a second component having a second interface portion with a textured surface to interface with the first interface portion and form a skeletal joint. The textured surface can include a plurality of concave features. Each of the concave features can be configured to compress a lubricant to facilitate hydrodynamic lubrication between the first and second interface portions to minimize wear between the first interface portion and the second interface portion of the prosthetic joint.

In one aspect, a method of facilitating use of a prosthetic joint is disclosed. The method can comprise providing a first component having a first interface portion. The method can also comprise providing a second component having a second interface portion to interface with the first interface portion and form a skeletal joint. Additionally, the method can comprise facilitating hydrodynamic lubrication between the first and second interface portions by compressing a lubricant to minimize wear between the first interface portion and the second interface portion of the prosthetic joint with a textured surface having a plurality of concave features.

Figure 1:
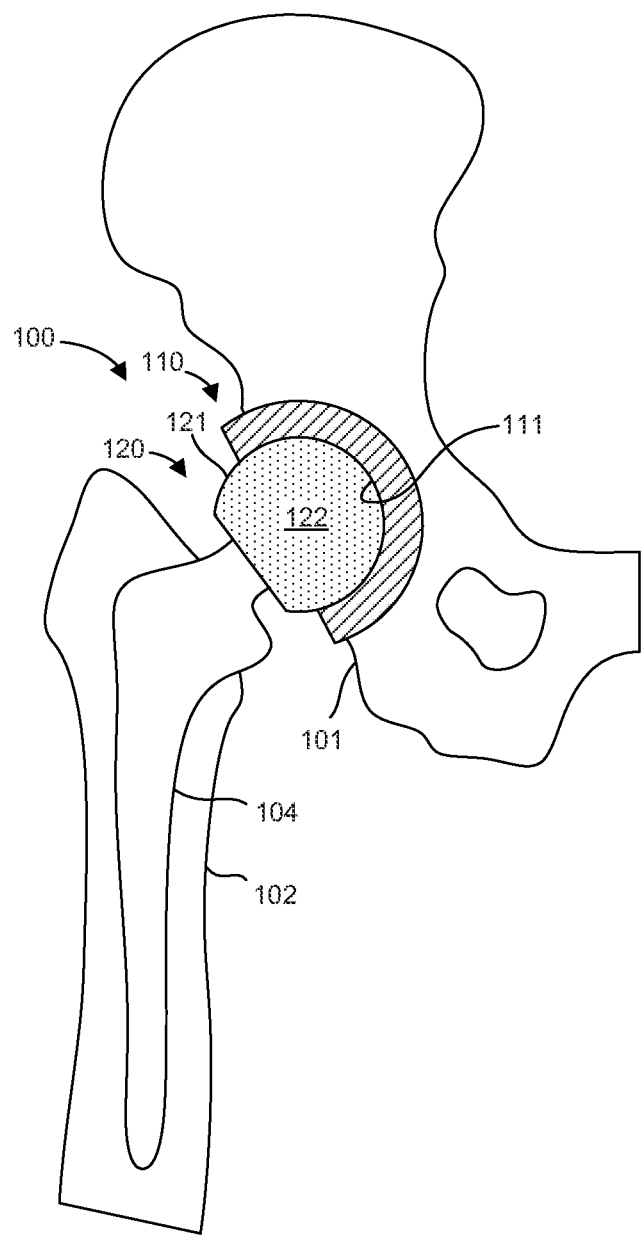
FIG. 1 is a perspective view of a prosthetic hip joint, in accordance with an example of the present disclosure.

These figures are provided merely for convenience in describing specific embodiments of the invention. Alteration in dimension, materials, and the like, including substitution, elimination, or addition of components can also be made consistent with the following description and associated claims. Reference will now be made to the exemplary embodiments illustrated, and specific language will be used herein to describe the same. It will nevertheless be understood that no limitation of the scope of the invention is thereby intended.

DETAILED DESCRIPTION

Reference will now be made to certain examples, and specific language will be used herein to describe the same. Examples discussed herein set forth a prosthetic joint and associated methods that can provide for reduced wear over typical prosthetic joints.

With the general embodiments set forth above, it is noted that when describing a prosthetic joint, or the related method, each of these descriptions are considered applicable to the other, whether or not they are explicitly discussed in the context of that embodiment. For example, in discussing the prosthetic joint per se, the system and/or method embodiments are also included in such discussions, and vice versa.

It is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a concave feature" includes one or more of such features and reference to "a textured surface" includes one or more of such surfaces.

Also, it is noted that various modifications and combinations can be derived from the present disclosure and illustrations, and as such, the following figures should not be considered limiting.

In describing and claiming the present invention, the following terminology will be used in accordance with the definitions set forth below.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "concave" refers to an inward depression which can include curved or flat inner walls.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a distance range of about 1 to about 20 mm should be interpreted to include not only the explicitly recited limits of about 1 mm and about 20 mm, but also to include individual lengths such as 2 mm, 11 mm, 14 mm, and sub-ranges such as 10 mm to 20 mm, 5 mm to 15 mm, etc.

Any steps recited in any method or process claims may be executed in any order and are not limited to the order presented in the claims unless otherwise stated. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Illustrated in FIG. 1 is a prosthetic hip joint 100. In accordance with one example of the present disclosure, the prosthetic joint can comprise a first component 110 and a second component 120 configured to interface with one another to form a skeletal joint. Accordingly, the first component can have a first interface portion 111 and the second component can have a second interface portion 121. As discussed in more detail herein, the second interface portion can include a textured surface 122 to interface with the first interface portion to minimize wear between the first interface portion and the second interface portion of the prosthetic joint. The prosthetic joint of the present disclosure can be configured as an implant for any human or animal joint, such as, but not limited to, a hip joint, a knee joint, an ankle joint, or a shoulder joint.

In one embodiment, the prosthetic joint 100 can comprise a hip joint, which can be used, for example, as a total hip replacement. In this case, the first component 110 can comprise an acetabular component to couple with an acetabulum (hip socket) 101 and the first interface portion 111 can comprise an acetabular cup. The second component 120 can comprise a femoral component to couple with a femur (thigh bone) 102 and the second interface portion 121 can comprise a femoral head. The acetabular cup can be placed into the acetabulum. Typically, cartilage and bone are removed from the acetabulum and the acetabular cup is attached using frictional interference fit and/or cement. The acetabular cup can comprise only a single piece, or multiple pieces of a modular construction. A one piece (monobloc) shell can have an articular surface machined on the inside surface of the cup and can optionally rely on cement or a capturing mechanism to hold a liner in place. A monobloc polyethylene cup can be cemented in place. A modular cup can have two pieces—a shell and liner. An outside of the shell can have a porous coating while an inside of the shell can contain a locking mechanism designed to accept a liner. A porous coating can be used to form a friction fit, such as a sintered bead or a foam metal, designed to mimic the trabeculae of cancellous bone. Additional fixation can be achieved as bone grows onto or into the porous coating. Screws can be used to lag the shell to the bone providing more secure fixation, especially during initial healing and bone bonding stages. A liner can be placed into the shell and connected by a rim locking mechanism or with a Morse taper. Although a variety of materials can be used, the liner can be formed of materials such as, but not limited to, ultra-high molecular weight polyethylene (UHMWPE), (highly) cross-linked polyethylene (XLPE), each of which can potentially be infused with vitamin E, and the like. The porous coating interfaces with surrounding bone and can be formed of materials such as, but not limited to, titanium, stainless steel, cobalt chromium, ceramic materials, and the like.

The femoral component 120 can be configured to fit in the femur 102. Typically, bone is removed and the femur is shaped to accept the femoral stem 104 of the implant with attached prosthetic femoral head. The femoral stem can be attached to the femur in any suitable manner. In one aspect, acrylic bone cement can form a mantle between the stem and the bone. Uncemented stems can use friction, shape, and/or surface coatings to stimulate bone to remodel and bond to the implant. Stems can be made of any suitable material, such as titanium, cobalt chromium, and stainless steel, and can be monolithic or modular. Modular components can comprise different head dimensions and/or modular neck orientations, which can attach via a taper similar to a Morse taper. These options allow for variability in leg length and offset.

An articular interface is the region between the acetabular cup and femoral head. The articular interface of the hip comprises a simple ball and socket joint. A size of the articular interface can be selected to optimize implant function and longevity while mitigating associated risks. The interface size is measured by the outside diameter of the head or the inside diameter of the socket. The prosthetic joint can include components of any suitable size. Common sizes of femoral heads are 28 mm, 32 mm and 36 mm, and even larger sizes of 38 mm to greater than 54 mm are contemplated. Larger diameter heads can lead to increased stability and range of motion while lowering the risk of dislocation; however, they may also be subject to higher friction and inertia.

In one aspect, the first interface portion 111 can be made of a polymer, such as polyethylene, polyetheretherketone, or combinations thereof, or any other suitable polymer. In a particular aspect, the first interface portion can be made of Ultra High Molecular Weight Polyethylene (UHMWPE) or cross-linked polyethylene (XLPE), both of which may be infused with vitamin E to improve oxidation resistance. In another aspect, the second interface portion 121 can be made of a metal. For example, the metal can comprise cobalt, chrome, titanium, nickel, iron, molybdenum, zirconium, aluminum, alloys thereof, combinations thereof, or any other suitable metal. In a particular aspect, the second interface portion can be made of cobalt chromium. In yet another aspect, the second interface portion can be made of a ceramic. Examples include oxides, nitrides, and borides of various metals such as, but not limited to, zirconium dioxide, aluminum oxide, titanium boride, or combinations thereof, or any other suitable ceramic. Other suitable interface materials can include, but are not limited to, diamond, diamond-like carbon, boron nitride, carbon nitride, and the like. It is noted that various combinations of metal-metal, metal-ceramic, ceramic-ceramic, ceramic-polymer, metal-polymer, and polymer-polymer combinations can be formed between the first and second interface portions. Furthermore, the respective interface portions can be formed as a continuous homogeneous body with the implant or can be a composite implant (e.g. a metal coating over a ceramic base).

Figure 2:
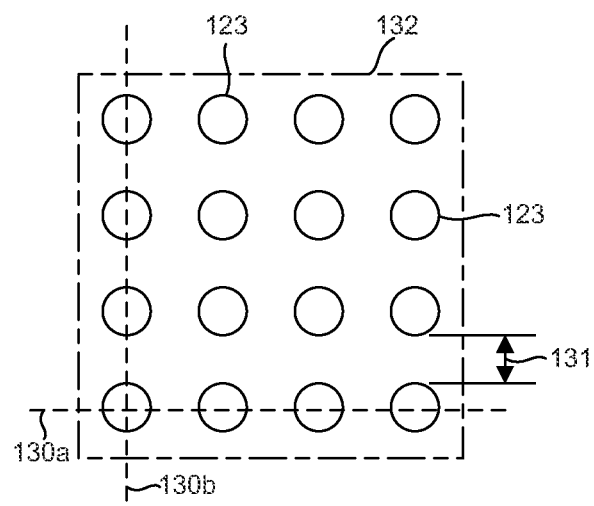
FIG. 2 is a top view of a plurality of concave features of a textured interface portion of the prosthetic hip joint of FIG. 1, in accordance with an example of the present disclosure.

With reference to FIG. 2, and continued reference to FIG. 1, the textured surface can include a plurality of concave features 123 or "dimples" to facilitate hydrodynamic lubrication between the first and second interface portions 111, 121 to minimize wear between the first interface portion and the second interface portion of the prosthetic joint 100. In one aspect, the plurality of concave features can comprise an array of concave features in a predetermined pattern, such as a grid pattern. Any suitable grid pattern may be utilized. In one example, shown in FIG. 2, the grid pattern can form a right angle between two intersecting lines 130a, 130b connecting adjacent concave features. In another example, the grid pattern can form an acute angle between two intersecting lines connecting adjacent concave features. In this case, adjacent rows of the grid may be "offset" from one another. It should be recognized that any suitable predetermined arrangement of concave features is contemplated and the present disclosure is not to be limited to regular non-random grid patterns. For example, in another aspect, an arrangement of the concave features can be random. Spacing 131 between the concave features in the predetermined pattern can therefore comprise uniform spacing, non-uniform spacing, or combinations thereof. In one aspect, an area density of the plurality of concave features 123 can be between about 10% and about 50% (i.e. a total area of a projection of the concave features 123 within an area of a geometric contour perimeter 132). In some embodiments, this can create a dense array of micro-sized concave features. Although a regular array of features can be used, non-uniform patterns can also be useful. For example, variations in feature geometry and spacing can be provided to different areas of the surface. In such cases, regions of high feature density and lower feature density can be utilized. In one aspect, the concave features can be substantially the same size and/or shape. The concave features can be manufactured on a surface using laser surface texturing (LST). However, these features can also be formed in any suitable manner such as, but not limited to, molding, vibro-mechanical texturing, chemical etching, and the like.

Figure 3:
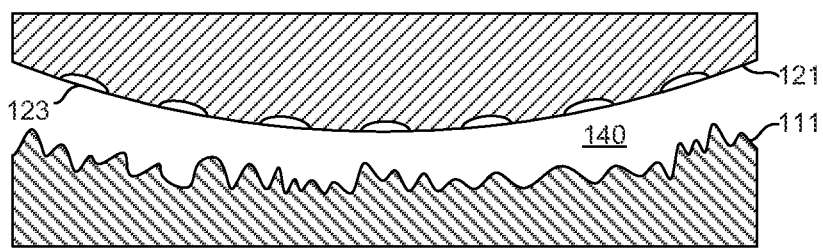
FIG. 3 is a cross-sectional representation of the interface portions of the prosthetic hip joint of FIG. 1, in accordance with an example of the present disclosure.

With reference to FIG. 3, and continued reference to FIGS. 1 and 2, the concave features 123 can be configured to facilitate hydrodynamic lubrication between the first and second interface portions 111, 121. The scale of the surface roughness as well as the concave features is exaggerated for the purpose of clarity. In a typical smooth prosthetic joint, asperities on both interface surfaces tend to be in contact, which can contribute to the formation of wear particles. In contrast to a typical smooth joint, FIG. 3 illustrates a femoral head textured with concave features. Hydrodynamic lubrication between sliding surfaces at low sliding velocities can prevent asperities of the surfaces from contacting each other, thus, preventing or minimizing production of wear particles that may cause the implant to fail over time.

In particular, the concave features 123 can be configured to compress a lubricant 140, such as synovial fluid between the first and second interface portions 111, 121 in relative motion. The compressed lubricant can generate a pressure between the first and second interface portions, which can cause and/or maintain separation of the interface portions. In other words, the concave features can cause separation of the interface portions by creating a fluid film bearing, due to the compression of the lubricant by the concave features, between the sliding components. The pressure created by the concave features can separate the femoral head and acetabular cup, for example, therefore minimizing asperity contact and reducing friction and wear. The concave features can create hydrodynamic lubrication at hip joint sliding velocities and, thus, reduce the formation of wear particles that eventually lead to failure of the implant. The concave features can significantly improve lubrication conditions between the sliding components of the prosthetic joint over typical smooth joint interfaces, which can significantly reduce wear rate and increase useful life of the joint.

Figure 4A:
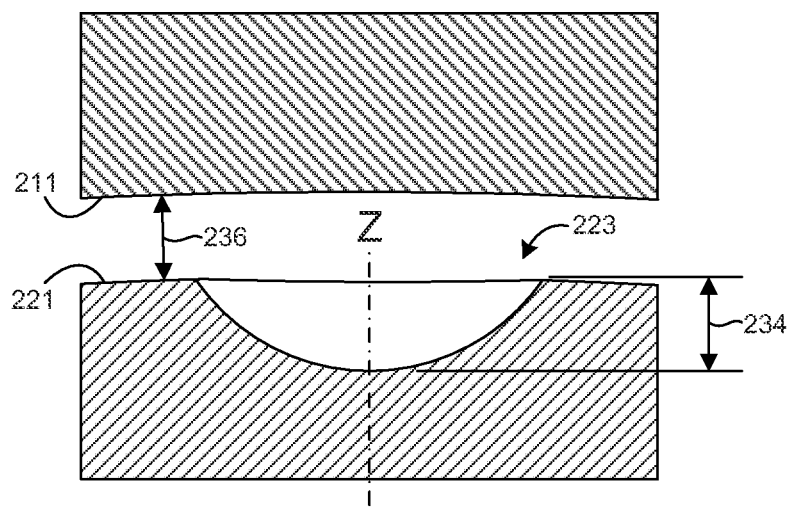
FIG. 4A is a cross-sectional representation of a concave feature of a textured interface portion of a prosthetic joint, in accordance with an example of the present disclosure.
Figure 4B:
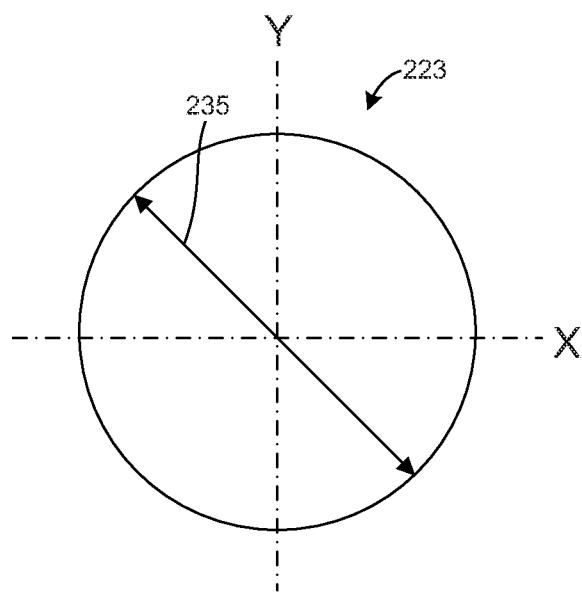
FIG. 4B is a top view of the concave feature of FIG. 4A.

FIGS. 4A and 4B illustrate a concave feature 223 in accordance with the present disclosure. Although dimensions can vary somewhat, a depth 234 of the concave feature can most often be between about 0.5 micrometer and about 2 micrometers. In one aspect, the depth can be between about 0.8 micrometer and about 1.2 micrometers, with 1 micrometer being typical. A width or diameter 235 of the concave feature can generally be between about 50 micrometers and about 200 micrometers. In one aspect, the width or diameter can be between about 80 micrometers and about 120 micrometers, with 100 micrometers being typical. The concave feature can have a depth to width aspect ratio of between about 0.005 and about 0.02. In one aspect, the aspect ratio can be between about 0.008 and about 0.012, with 0.01 being typical. The shallow concave feature relative to the width can be beneficial to compress lubricant in the joint and create the bearing pressure that causes separation of the moving interface portions 211, 221 or bearing surfaces, which can increase the bearing spacing 236 or distance between the mating interface portions for a given load and reduce asperity contact. In other words, the shallow concave feature can increase load carrying capacity and reduce friction that causes wear and improve the durability of the articulating bearing.

In another aspect, the concave feature 223 can be axis-symmetric to accommodate non-symmetric gait kinematics. For example, the concave feature can be symmetric about the Z axis, which can be oriented normal to an outer surface of the interface portion 221 and/or radially oriented from a center of the interface portion. In its simplest form, hip kinematics follows a reciprocating linear motion so a feature or texture, if non-symmetric, may help in one direction and harm in the other. For example, a non-symmetric feature would generate a different pressure depending on the sliding direction. An axis-symmetric concave feature can provide effective lubricant compression by the concave feature that is independent of the direction of relative motion between the interface portions 211, 221. Axis-symmetric concave features can be beneficial in this regard because actual joint or hip kinematics are not symmetric. The axis-symmetric concave features can therefore also facilitate maximizing bearing spacing 236 over the entire gait cycle. By creating hydrodynamic lubrication over a maximum portion of the gait cycle, the technology of the present disclosure can effectively function throughout the life of the prosthetic joint, not just the beginning of life. Thus, the prosthetic joint can improve the comfort of millions of patients over a long term and reduce health care costs.

Figure 5A:
FIGS. 5A-5F are cross-sectional representations of concave features of textured interface portions of prosthetic joints, in accordance with several examples of the present disclosure.
Figure 5B:
Figure 5C:
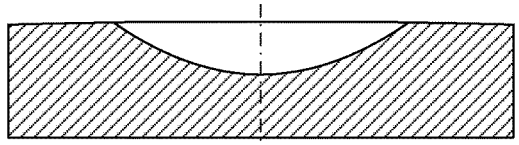
Figure 5D:
Figure 5E:
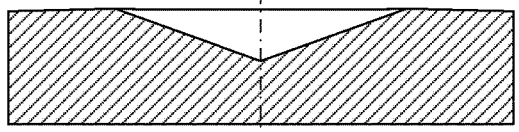
Figure 5F:

Other examples of axis-symmetric concave features in accordance with the present disclosure are shown in FIGS. 5A-5F. For example, FIG. 5A illustrates a concave feature 323 with a shape defined at least in part by a sphere, the cross-sectional shape being circular or arcuate. FIG. 5B illustrates a concave feature 423 with a shape defined at least in part by a spheroid or circular ellipsoid, the cross-sectional shape being elliptical segment. FIG. 5C illustrates a concave feature 523 with a shape defined at least in part by a circular paraboloid, the cross-sectional shape being parabolic. FIG. 5D illustrates a concave feature 623 with a shape defined at least in part by a circular hyperboloid, the cross-sectional shape being hyperbolic. FIG. 5E illustrates a concave feature 723 with a shape defined at least in part by a circular cone, the cross-sectional shape being triangular. FIG. 5F illustrates a concave feature 823 with a shape defined at least in part by a circular cylinder, the cross-sectional shape being rectangular. It should therefore be recognized that the concave features can be of any suitable size and/or shape or combinations of shapes that, in one aspect, can be axis-symmetric. In another aspect, the concave features can form micro-scale reservoirs allow compression of the lubricant rather than redistribute lubricant or trap wear particles.

Although cross-linked polyethylene material has recently been successfully implemented to reduce polyethylene wear, even cross-linked polymers have been observed to cause osteolysis. The concave features, by reducing friction, can exhibit similar wear performance to that achieved by radiation-induced cross-linking of polyethylene material. This can potentially obviate the need for cross-linked polyethylene, which is inferior in strength and fatigue endurance compared to traditional UHMWPE. Thus, concave features can serve to benefit durability of the joint against abrasive/adhesive wear as well as against fatigue-evoked pitting and delamination, to which cross-linked polyethylene may be susceptible.

In a related example, and to reiterate to some degree, a method of facilitating use of a prosthetic joint is presented in accordance with the principles herein. The method can comprise providing a first component having a first interface portion. The method can also comprise providing a second component having a second interface portion to interface with the first interface portion and form a skeletal joint. In addition, the method can comprise facilitating hydrodynamic lubrication between the first and second interface portions by compressing a lubricant to minimize wear between the first interface portion and the second interface portion of the prosthetic joint with a textured surface having a plurality of concave features. It is noted that no specific order is required in this method, though generally in one embodiment, these method steps can be carried out sequentially.

In one aspect, the second interface portion can comprise a textured surface having a plurality of concave features, each of the concave features being configured to compress the lubricant. In another aspect, the method can further comprise optimizing the textured surface for a given patient based on at least one of a weight of the patient and activity level of the patient. In a particular aspect of the method, optimizing the textured surface can comprise optimizing a pattern of the plurality of concave features and geometry of individual features. High-activity patients and low-activity patients can benefit from different texture geometry and features, since the operating conditions of the bearing interface can be significantly different for these patients. For instance, a high-activity patient may run, cycle, or ski, which creates different joint kinematics than in a low-activity patient that only walks. As such, the texture geometry and pattern can be designed to accommodate these vastly different operating conditions. In another particular aspect of the method, optimizing the textured surface can comprise optimizing at least one of a size and a shape of the plurality of concave features.

It is to be understood that the above-referenced embodiments are illustrative of the application for the principles of the present invention. Numerous modifications and alternative arrangements can be devised without departing from the spirit and scope of the present invention while the present invention has been shown in the drawings and described above in connection with the exemplary embodiment(s) of the invention. It will be apparent to those of ordinary skill in the art that numerous modifications can be made without departing from the principles and concepts of the invention as set forth in the claims.

What is claimed is:

1. A prosthetic joint, comprising:
   a first component having a first interface portion; and
   a second component having a second interface portion with a textured surface to interface with the first interface portion and form a skeletal joint,
   wherein the first interface portion comprises at least one of a metal and a ceramic, and the second interface portion comprises a polymer, and
   wherein the textured surface includes a plurality of concave features, each of the concave features being configured to compress a lubricant to facilitate hydrodynamic lubrication during use between the first and second interface portions to minimize wear between the first interface portion and the second interface portion of the prosthetic joint, and wherein each of the concave features has a depth to width aspect ratio of between 0.005 and 0.02.

2. The prosthetic joint of claim 1, wherein a depth of each of the concave features is between 0.5 micrometers and 2 micrometers.

3. The prosthetic joint of claim 1, wherein a width of each of the concave features is between 50 micrometers and 200 micrometers.

4. The prosthetic joint of claim 1, wherein a shape of each of the concave features is axis-symmetric.

5. The prosthetic joint of claim 4, wherein the shape is defined at least in part by a sphere.

6. The prosthetic joint of claim 1, wherein the plurality of concave features comprises an array of concave features in a predetermined pattern.

7. The prosthetic joint of claim 6, wherein the predetermined pattern comprises uniform spacing between the plurality of concave features.

8. The prosthetic joint of claim 1, wherein an area density of the plurality of concave features on the second interface portion is between 10% and 50%.

9. The prosthetic joint of claim 1, wherein the plurality of concave features are substantially the same size and shape.

10. The prosthetic joint of claim 1, wherein the first component comprises an acetabular component to couple with an acetabulum and the first interface portion comprises an acetabular cup, and wherein the second component comprises a femoral component to couple with a femur and the second interface portion comprises a femoral head.

11. The prosthetic joint of claim 1, wherein the metal comprises cobalt, chrome, titanium, nickel, iron, molybdenum, zirconium, aluminum, or combinations thereof.

12. The prosthetic joint of claim 1, wherein the ceramic comprises zirconium dioxide, aluminum oxide, or combinations thereof.

13. The prosthetic joint of claim 1, wherein the polymer comprises polyethylene, polyetheretherketone, or combinations thereof.

14. A method of facilitating use of a prosthetic joint, comprising:
    providing a first component having a first interface portion;
    providing a second component having a second interface portion with a textured surface having a plurality of concave features to interface with the first interface portion and form a skeletal joint, wherein the first interface portion comprises at least one of a metal and a ceramic, and the second interface portion comprises a polymer, and where each of the plurality of concave features has a depth to width aspect ratio of between 0.005 and 0.02; and
    facilitating hydrodynamic lubrication between the first and second interface portions during use by compressing a lubricant to minimize wear between the first interface portion and the second interface portion of the prosthetic joint.

15. The method of claim 14, wherein the second interface portion comprises the textured surface having the plurality of concave features, each of the concave features being configured to compress the lubricant.

16. The method of claim 14, further comprising optimizing the textured surface for a given patient based on at least one of a weight of the patient and activity level of the patient.

17. The method of claim 16, wherein optimizing the textured surface comprises optimizing a pattern of the plurality of concave features.

18. The method of claim 16, wherein optimizing the textured surface comprises optimizing at least one of a size and a shape of the plurality of concave features.

* * * * *